(12) United States Patent
Wu et al.

(10) Patent No.: US 9,460,054 B2
(45) Date of Patent: Oct. 4, 2016

(54) METHOD FOR DETECTING ELECTROMAGNETIC PROPERTY OF ORIENTED SILICON STEEL

(75) Inventors: Meihong Wu, Shanghai (CN); Weizhong Jin, Shanghai (CN); Huande Sun, Shanghai (CN); Guohua Yang, Shanghai (CN); Kanyi Shen, Shanghai (CN); Jie Huang, Shanghai (CN); Guobao Li, Shanghai (CN)

(73) Assignee: BAOSHAN IRON & STEEL CO., LTD., Shanghai (CN)

( * ) Notice: Subject to any disclaimer, the term of this patent is extended or adjusted under 35 U.S.C. 154(b) by 537 days.

(21) Appl. No.: 13/643,371

(22) PCT Filed: Apr. 12, 2011

(86) PCT No.: PCT/CN2011/072644
§ 371 (c)(1),
(2), (4) Date: Oct. 25, 2012

(87) PCT Pub. No.: WO2011/160482
PCT Pub. Date: Dec. 29, 2011

(65) Prior Publication Data
US 2013/0090876 A1 Apr. 11, 2013

(30) Foreign Application Priority Data
Jun. 22, 2010 (CN) .......................... 2010 1 0207498

(51) Int. Cl.
*G06F 17/13* (2006.01)
*G01N 27/72* (2006.01)
*G01R 33/00* (2006.01)

(52) U.S. Cl.
CPC ............... *G06F 17/13* (2013.01); *G01N 27/72* (2013.01); *G01R 33/0064* (2013.01)

(58) Field of Classification Search
CPC .. G01R 33/0064; G01N 27/72; G01N 33/20; G06F 17/13
See application file for complete search history.

(56) References Cited

U.S. PATENT DOCUMENTS 5,365,170 A  11/1994  Beckley

FOREIGN PATENT DOCUMENTS

CN  101114011 A  1/2008
CN  101210947 A  7/2008
(Continued)

OTHER PUBLICATIONS

Kitae Lee, Quantitative Analysis of Texture Development in Fe-3%Si During Secondary Recrystallization, Jul. 1993, Master of Engineering Thesis, Department of Mining and Metallurgical Engineering, McGill University, Montreal, Canada, 141 pp.*
(Continued)

*Primary Examiner* — Toan Le
(74) *Attorney, Agent, or Firm* — Quarles & Brady, LLP

(57) ABSTRACT

A method for detecting electromagnetic property of oriented silicon steel, the method comprises: measuring Euler angles of each of crystal grains in a specimen by use of metallographic etch-pit method; calculating orientation deviation angle $\theta_i$ (degree) of the crystal grain; combining area Si ($mm^2$) of the crystal grain and correction coefficient X of element Si (X=0.1~10 T/degree); correcting on the basis of the magnetic property $B_0$ (saturation magnetic induction, T) of single-crystal material by using these parameters ($\theta_i$, $S_i$, X), formula for correcting is $$B_8 = -0.015 \times X \times \frac{\sum_{n=1}^{i} S_i|\theta_i|}{\sum_{n=1}^{i} S_i} + (B_0 - 0.04) \quad (1)$$

obtaining electromagnetic property $B_8$ of the oriented silicon steel by the above calculations. The present invention can implement detection of electromagnetic property of a specimen under the circumstances that there is no magnetizm measuring device or that magnetizm measuring devices cannot be used due to reasons such as weight and size of the specimen being too small or surface quality of the specimen being poor.

1 Claim, 3 Drawing Sheets

(56) References Cited

FOREIGN PATENT DOCUMENTS

CN    101216440       7/2008
JP    2002-156361 A   5/2002

OTHER PUBLICATIONS

International Search Report under date of mailing of Jul. 21, 2011 in connection with PCT/CN2011/072644.
Kumano et al., The Relationship between Primary and Secondary Recystallization Texture of Grain Oriented Silicon Steel; ISIJ International ( 2002) vol. 42, No. 4, pp. 440-449.
Lee et al., The Application of the Etch-Pit Method to Quantitative Texture Analysis; Journal of Materials Science (1995) vol. 30, pp. 1327-1332.
Ushigami et al., Mechanism of Orientation Selectivity During Grain Growth of Secondary Recrystallization in Fe-3%Si Alloy; Textures and Microstructures; vol. 32, pp. 137-151, 1999.
Liu et al., ODF Determination of the Recrystallization Texture of Grain Oriented Silicon Steel from the Etch Figure; Journal of Northeastern University (Natural Science) (1997) vol. 6, p. 614.
Zhou et al., A Study on the Deformation and Primary Recrystallization Texture in a MnS—AlN-Inhibited 3% Silicon Steel; Acta Metall Sin (1981) vol. 17, No. 1, p. 58.
Luo, Y., Formation Conditions and Geometric Diversity of Etched Pits; Acta Metall Sin (1982) vol. 18, No. 4, p. 472.
He, Zhongzhi, Electric Steel, Metallurgical Industry Press (1996) Beijing.

* cited by examiner

METHOD FOR DETECTING ELECTROMAGNETIC PROPERTY OF ORIENTED SILICON STEEL

CROSS-REFERENCE TO RELATED APPLICATIONS

This application represents the national stage entry of PCT International Application No. PCT/CN2011/072644 filed on Apr. 12, 2011 and claims the benefit of Chinese Patent Application No. 201010207498.0 filed Jun. 22, 2010. The contents of both of these applications are hereby incorporated by reference as if set forth in their entirety herein.

FIELD OF THE INVENTION

This invention relates generally to a detection method, and particularly to a method for detecting electromagnetic property of oriented silicon steel.

BACKGROUND

Epstein's square and circle method is stipulated by Chinese national standard (GB/T 3655-2000) as a method for detecting magnetic property of electric steel, which has strict requirements on weight, surface quality and so on of specimens. In the case that a specimen has too small weight and poor surface quality, it is impossible to use the Epstein's square and circle method to measure magnetic property (GB/T 3655-2000 requirements: effective mass of a specimen shall be at least 240 g, length of a specimen is recommended to be 300 mm, mass is about 1 kg; shear requirements of a specimen lie in that the shear shall be orderly, flat, being of good right-angle, and having no obvious burrs on the edge).

Etch pits are formed by preferential corrosion performed on crystal face of specimen surface. By use of this characteristic, it is possible to use metallographic etch-pit method to directly calculate crystallographic orientation of each crystal grain in the specimen (see "FORMATION CONDITIONS AND GEOMETRIC DIVERSITY OF ETCHED PITS", Y. Luo, Acta metall Sin, 1982, 18 (4), p 472; "A STUDY ON THE DEFORMATION AND PRIMARY RECRYSTALLIZATION TEXTURE IN A MnS—AlN-INHIBITED 3% SILICON STEEL", Q. C. Lv, R. J. Shuai, X. Y. Zhou et. al., Acta Metall Sin, 1981, 17 (1), p 58); "The application of the etch-pit method to quantitative texture analysis", K. T. LEE, G. de WIT, A. MORA WIEC, J. A. SZPUNAR, JOURNAL OF MATERIAL SCIENCE, 1995, 30, p 1327-1332), and then to calculate orientation deviation angle $\theta_i$ of the crystal grain (see "ODF Determination of the Recrystallization Texture of Grain Oriented Silicon Steel from the Etch Figure", G. Liu, F. Wang et. al., Journal of Northeastern University (Natural Science), 1997, 18 (6), p 614; "The application of the etch-pit method to quantitative texture analysis", K. T. LEE, G. de WIT, A. MORA WIEC, J. A. SZPUNAR, JOURNAL OF MATERIAL SCIENCE, 1995, 30, p 1327-1332).

Magnetocrystalline anisotropy is a phenomenon due to a coupling effect between electron orbit and magnetic moment as one party and crystal lattice as another party, which makes magnetic moment have an optimum-choosing arrangement along a certain crystallographic axis, so as to result in difference of magnetization characteristics in various crystallographic axis directions. Crystallographic axis <100> is an easy magnetization direction, crystallographic axis <111> is a hard magnetization direction, and crystallographic axis <110> falls in between. As to oriented silicon steel, its electromagnetic property is closely related to crystal grain orientation <100> of a specimen (see "Electric Steel", H E Zhongzhi, Metallurgical Industry Press, Beijing, 1996; "Mechanism of Orientation Selectivity of Secondary Recrystallization in Fe-3% Si Alloy", Yoshiyuki USHIGAMI, Takeshi KUBOTA and Nobuyuki TAKAHASHI, Textures and Microstructures, vol. 32, p 137-151; "The Relationship between Primary and Secondary Recrystallization Texture of Grain Oriented Silicon Steel", Tomoji KUMANO, Tsutomu HARATANI and Yoshiyuki USHIGAMI, ISIJ International, 2002, 42(4) 440). In view of the above, it is possible to use the metallographic pit-etching method plus calculation formula to take the place of magnetism-measuring devices to detect electromagnetic property of oriented silicon steel, as an innovative solution, which has the advantage that it can detect electromagnetic property in the cases that Epstein's square and circle method is not applicable thereto, such as specimen's weight being too small or its surface quality being poor.

In Chinese patent (Publication No.: CN101216440A), this invention utilizes a unsymmetrical X-ray diffraction method by using a fixed angle 2θ to perform ω can, in order to determine distribution of lattice orientation in the easy magnetization direction [001] of oriented silicon steel. A shortcoming of this patent, however, lies in that only deviation angle of lattice orientation [001] of the finished oriented silicon steel product is measured, but not further studying relativity between deviation angle of lattice orientation [001] and magnetism of the oriented silicon steel product.

In Chinese patent (Publication No.: CN101210947A), this invention measures three Euler angles of lattice orientation at every point of a specimen by use of EBSD system and accounts ratio X in every same or similar lattice orientation, and then calculates reckoned thickness coefficient $f_H$, composition $f_C$ and influence coefficient e of orientation difference on performance. Magnetic property B of the specimen is obtained by correcting these coefficients based on pure iron performance $B^\theta$. However, this patent has the following shortcomings: firstly, since EBSD device is expensive and is cumbersome in operation, many enterprises, especially small and medium-sized ones, are not able to apply this technique; secondly, with regards to calculation model for magnetic property of a finished product, it has been found from experimental data (oriented silicon steel with thickness 0.2~0.3 mm) that thickness has little impact on magnetic property of the finished product, and it has been found from researches on chemical compositions that Si is a predominant influencing factor, and other chemical compositions have a little or basically no influence.

SUMMARY

The object of the invention is to provide a method to detect electromagnetic property of oriented silicon steel, which can implement detection of electromagnetic property of a specimen under the circumstances that there is no magnetism measuring device or that magnetism measuring devices cannot be used due to reasons such as weight and size of the specimen being too small or surface quality of the specimen being poor.

In order to attain the object, solution of the invention is as follows.

The present invention utilizes metallographic etch-pit method to measure Euler angles (α, β, γ) of each of crystal grains in a specimen of a finished product. Euler angles (α, β, γ) are a group of three independent angle parameters used to determine position of a fixed-point rotation rigid body, which consists of angle of nutation α, angle of precession β and angle of rotation γ. An orientation deviation angle $θ_i$ of the crystal grain is then converted out from the Euler angles (α,β,γ), and finally, the electromagnetic property of the specimen can be calculated by use of other related parameters.

In particular, the invention provides a method for detecting electromagnetic property of oriented silicon steel, which comprises: measuring Euler angles of each of crystal grains in a specimen by use of metallographic etch-pit method; calculating orientation deviation angle $θ_i$ (degree) of the crystal grain; combining area $S_i$ (mm$^2$) of the crystal grain and correction coefficient X of element $S_i$ (X=0.1~10 T/degree); correcting on the basis of magnetic property $B_0$ (saturation induction density, T) of single crystal material, by using these parameters ($θ_i$, $S_i$, X), formula for correcting is $$B_8 = -0.015 \times X \times \frac{\sum_{n=1}^{i} S_i|θ_i|}{\sum_{n=1}^{i} S_i} + (B_0 - 0.04) \quad (1)$$

The electromagnetic property $B_8$ of the oriented silicon steel is obtained by the above calculations.

For specimens of a finished oriented silicon steel product with the same thickness, it can be calculated from formula (1) that an interrelation illustrated by formula 2 exists between average deviation angle θ and electromagnetic property $B_8$ of the finished sheet product. The average deviation angle θ is a weighted average of degree of orientation $θ_i$ of each macrograin (plus or minus sign merely denotes deviation of [001] lattice orientation to rolling direction from left side or right side) and area $S_i$ (see formula (2)).

$$θ = \frac{\sum_{n=1}^{i} S_i|θ_i|}{\sum_{n=1}^{i} S_i} \quad (2)$$

The present invention can implement detection of magnetic property of a specimen under the circumstances that there is no magnetism measuring device or that magnetism measuring devices cannot be used due to reasons such as weight and size of the specimen being too small or surface quality of the specimen being poor. At the same time, the method is capable to precisely detect magnetic property of any small region and thus is very suitable for laboratory research on magnetic materials, such as oriented silicon steels, and especially is representative for data of the same compositions.

Comparison of the Present Invention with the Prior Art:
the present invention utilizes a metallographic method that is more convenient to detect [001] crystal orientation deviation angle of finished oriented silicon steel sheet product, further studies relativity between the [001] crystal orientation deviation angle of the finished oriented silicon steel sheet product and magnetic property of the finished product, and finally obtains relational model of the deviation angle and the magnetic property of the finished product. And, the present invention might determine magnetic property of the finished product based on the deviation angle detected by the metallographic method.

By using the metallographic etch-pit method, the present invention overcomes shortcomings of EBSD technique, e.g., expensive devices and cumbersome operations, i.e., the invention is inexpensive and easy to use, as it might detect magnetic property of a specimen only with a metallographic microscope. Secondly, the present invention establishes a more suitable relational model between the deviation angle and the magnetic property of the finished product through experiments, so as to eliminate inoperative thickness coefficient and find out Si in chemical compositions has predominant effect on magnetic property of the finished product.

DETAILED DESCRIPTION

The invention provides a method for detecting electromagnetic property of oriented silicon steel, which utilizes a metallographic etch-pit method to measure Euler angles of each of crystal grains in a specimen of a finished product, and then utilizes the measured Euler angles to calculate comprehensive deviation angle $θ_i$ of orientation <100> of various crystal grains {110} in respect to rolling plane and rolling direction of the specimen, and meanwhile counts area $S_i$ to which each of the crystal grains corresponds.

Electromagnetic property of oriented silicon steel with 2.8% Si content is measured by using Epstein's square and circle method, and then electromagnetic properties of specimens, average deviation angles of which is identical to that of the specimen with 2.8% Si content but Si contents of which are 3.0%, 3.2%, 3.4%, 3.6% and 4.0%, are measured. Suppose that correction coefficient of electromagnetic property of the specimen with 2.8% Si content is 1, specimens with other Si contents, by comparing magnetic property thereof with that of the supposed specimen, obtain chemical composition correction coefficients X of different Si contents. Finally, a correction coefficient X for all compositions can be reckoned by fitting.

Electromagnetic property $B_8$ of a specimen can be calculated in accordance with following equation, in which $B_0$ is magnetic induction property of a single-crystal material:

$$B_8 = -0.015 \times X \times \frac{\sum_{n=1}^{i} S_i|θ_i|}{\sum_{n=1}^{i} S_i} + (B_0 - 0.04)$$

Embodiment 1

(1) An oriented silicon steel with 2.8% Si content is selected, which has thickness h=0.30 mm. SST (single sheet testing) detection is performed for electromagnetic property $B_8$(T).

Figure 3:
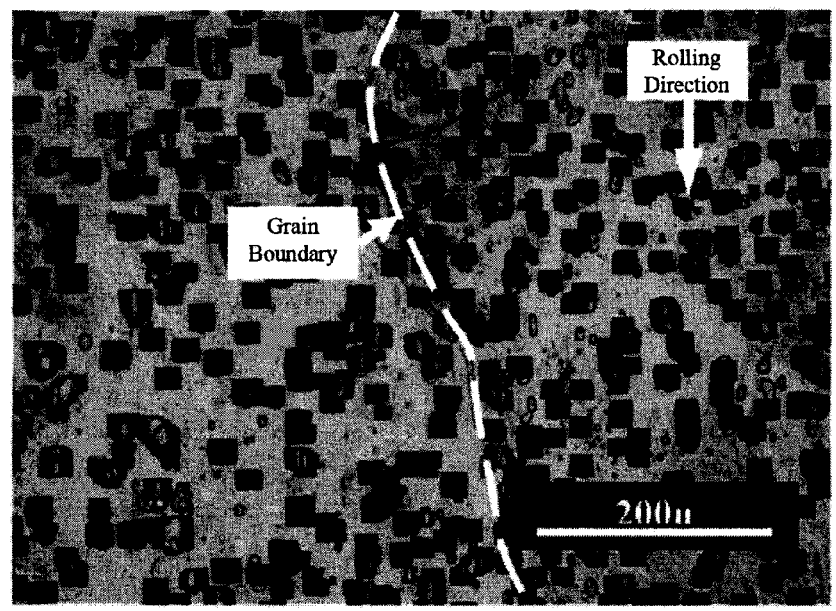
FIG. 3 is a photo of typical etch pits.

(2) After the detection of the electromagnetic property $B_8$, insulated coating on surface and bottom layer of the specimen is removed; then the specimen is etched by use of special etch-pit process so as to enable each of crystal grains to have a clear etched pit (refer to FIG. 3 for photo of typical etch pits); and based on parameters (shape, deviation angle of rolling direction, ratio of both sides of the etched pit, etc.) of respective etched pit of the crystal grains, Euler angles $(\alpha,\beta,\gamma)$ of the crystal grain are calculated.

(3) Miller index $\{HKL\}<UVW>$ of the crystal grain is reckoned by use of the Euler angles $(\alpha,\beta,\gamma)$ (calculation formulas are given in equations (3) and (4));

$$H:K:L = -\sin\beta\cos\gamma : \sin\beta\sin\gamma : \cos\beta \quad (3)$$

$$U:V:W = (\cos\beta\cos\alpha\cos\gamma - \sin\alpha\sin\gamma) : (-\cos\beta\cos\alpha\sin\gamma - \sin\alpha\cos\gamma) : \sin\beta\cos\alpha \quad (4)$$

Based on the Miller index, deviation angle $\theta_i$ with respect to (110)[001] is calculated (refer to equation (5));

$$\cos\theta = \frac{h_1 h_2 + k_1 k_2 + l_1 l_2}{\sqrt{(h_1^2 + k_1^2 + l_1^2)(h_2^2 + k_2^2 + l_2^2)}} \quad (5)$$

Figure 1:
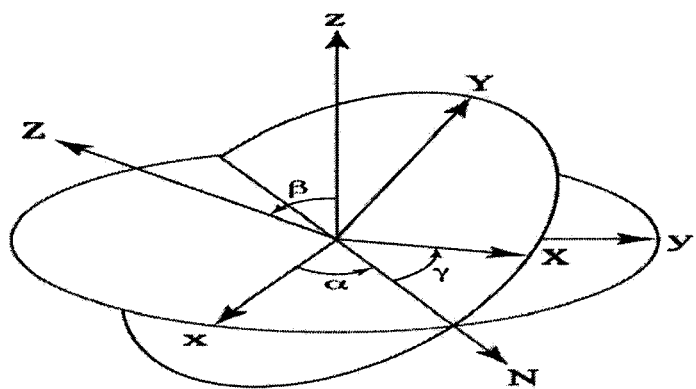
FIG. 1 is a schematic diagram of Euler angles.
Figure 2:
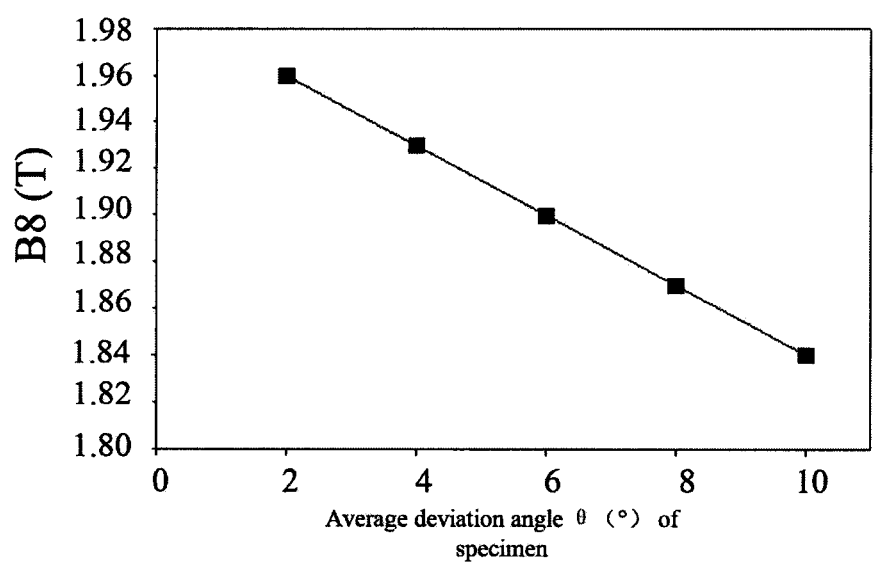
FIG. 2 illustrates relationship between average deviation angle θ and magnetic property $B_8$ of a specimen of a finished product of oriented silicon steel.

(4) Based on the deviation angle $\theta_i$ and corresponding area $S_i$ of the respective crystal grains in the specimen (refer to table 1), an average deviation angle of the specimen is calculated, and magnetic property $B_8$ of the specimen is reckoned from the equation 1 and FIG. 1, which is then compared to actual measured value (refer to the particulars in table 2).

TABLE 1 deviation angle $\theta_i$ (degree) and corresponding area $S_i$ (mm²) of 2# specimen

| No. | Angle | Area |
|---|---|---|
| 1 | 11 | 50 |
| 2 | 5 | 1320 |
| 3 | 0 | 141 |
| 4 | 9 | 30 |
| 5 | 16 | 25 |
| 6 | 3 | 450 |
| 7 | -11 | 99 |
| 8 | 0 | 120 |
| 9 | 4 | 44 |
| 10 | 4 | 1500 |
| 11 | -2 | 30 |
| 12 | 3 | 1000 |
| 13 | 12 | 200 |
| 14 | 0 | 1210 |
| 15 | -3 | 216 |
| 16 | 9 | 500 |
| 17 | 9 | 140 |
| 18 | 6 | 2750 |
| 19 | 0 | 196 |
| 20 | 10 | 35 |
| 21 | 2 | 96 |
| 22 | 3 | 121 |
| 23 | 0 | 30 |
| 24 | 0 | 56 |
| 25 | -2 | 1750 |
| 26 | 2 | 1080 |
| 27 | 3 | 90 |
| 28 | -2 | 1400 |
| 29 | -9 | 60 |
| 30 | 8 | 324 |
| 31 | 2 | 225 |
| 32 | 10 | 52 |
| 33 | 0 | 2000 |
| 34 | 2 | 660 |

$$\theta = \frac{\sum_{n=1}^{i} S_i |\theta_i|}{\sum_{n=1}^{i} S_i}$$

$$\theta = 3.3$$

Figure 4:
FIG. 4 illustrates the particulars and result of a specimen of embodiment 1 of the present invention (numbers labeled on crystal grains of the specimen are deviation angle $θ_i$ thereof).

See FIG. 4 and Table 2, the figure shows the particulars and result of the specimen of the embodiment 1 (numbers labeled on the crystal grains of the specimen are deviation angle $\theta_i$ of the crystal grains).

TABLE 2

| | |
|---|---|
| Measured value $B_8$ (T) | 1.95 |
| Calculated value $B_8$ (T) | 1.9405 |
| Deviation (%) | 0.5 |

As can be seen from the Table 2, deviation of magnetic property data detected by the present invention over magnetic property data detected by SST is 0.5%, which fully satisfies requirements for high precision detection.

Embodiment 2

(1) A specimen of an oriented silicon steel with 2.8% Si content and thickness h=0.27 mm is selected. An SST (single sheet testing) detection for electromagnetic property $B_8$ (T) is performed.

(2) After the detection of the electromagnetic property $B_8$, insulated coating and bottom layer on the surfaces of the specimen is removed; then the specimen is etched by use of special etch-pit process so as to enable each of crystal grains to have a clear etched pit (refer to FIG. 3 for photo of typical etch pits); and based on parameters (shape, deviation angle of rolling direction, ratio of both sides of the etched pit, etc.) of respective etched pit of the crystal grains, Euler angles $(\alpha,\beta,\gamma)$ of the crystal grain are calculated.

(3) Miller index $\{HKL\}<UVW>$ of the crystal grain is reckoned by use of the Euler angles $(\alpha,\beta,\gamma)$ (calculation formulas are given in equations (2) and (3));

$$H:K:L = -\sin\beta\cos\gamma : \sin\beta\sin\gamma : \cos\beta \quad (2)$$

$$U:V:W = (\cos\beta\cos\alpha\cos\gamma - \sin\alpha\sin\gamma) : (-\cos\beta\cos\alpha\sin\gamma - \sin\alpha\cos\gamma) : \sin\beta\cos\alpha \quad (3)$$

Based on the Miller index, deviation angle $\theta_i$ with respect to (110)[001] is reckoned (refer to equation (4));

$$\cos\theta = \frac{h_1 h_2 + k_1 k_2 + l_1 l_2}{\sqrt{(h_1^2 + k_1^2 + l_1^2)(h_2^2 + k_2^2 + l_2^2)}} \quad (4)$$

(4) Based on the deviation angle $\theta_i$ and corresponding area Si of the respective crystal grains in the specimen (refer to Table 3), an average deviation angle of the specimen is calculated, and magnetic property $B_8$ of the specimen is reckoned from the equation (1) and FIG. 1, which is then compared to actual measured value (refer to the particulars in table 3).

TABLE 3 deviation angle $\theta_i$ (degree) and corresponding area $S_i$ (mm$^2$) of the specimen

| No. | Angle | Area |
|---|---|---|
| 1 | −3 | 10 |
| 2 | 5 | 35 |
| 3 | 0 | 30 |
| 4 | 5 | 100 |
| 5 | 7 | 128 |
| 6 | 7 | 400 |
| 7 | 9 | 100 |
| 8 | 7 | 132 |
| 9 | −6 | 400 |
| 10 | −4 | 70 |
| 11 | 7 | 300 |
| 12 | −3 | 90 |
| 13 | 3 | 600 |
| 14 | 0 | 440 |
| 15 | −5 | 50 |
| 16 | 11 | 80 |
| 17 | 9 | 9 |
| 18 | 7 | 30 |
| 19 | 5 | 300 |
| 20 | −6 | 144 |
| 21 | −23 | 16 |
| 22 | −6 | 36 |
| 23 | 0 | 100 |
| 24 | 18 | 40 |
| 25 | 29 | 35 |
| 26 | −9 | 575 |
| 27 | 17 | 1200 |
| 28 | 7 | 91 |
| 29 | 3 | 125 |
| 30 | 10 | 40 |
| 31 | −10 | 20 |
| 32 | 2 | 18 |
| 33 | 0 | 50 |
| 34 | 4 | 124 |
| 35 | 0 | 40 |
| 36 | 12 | 120 |
| 37 | 0 | 255 |
| 38 | 22 | 144 |
| 39 | 17 | 15 |
| 40 | −4 | 300 |
| 41 | 17 | 63 |
| 42 | 5 | 230 |
| 43 | 6 | 450 |
| 44 | −42 | 48 |
| 45 | −8 | 28 |
| 46 | 42 | 15 |
| 47 | 27 | 50 |
| 48 | 0 | 300 |
| 49 | 38 | 274 |
| 50 | 10 | 51 |
| 51 | 7 | 78 |
| 52 | 20 | 226 |
| 53 | 0 | 150 |
| 54 | 14 | 144 |
| 55 | 12 | 80 |
| 56 | 13 | 140 |
| 57 | 11 | 70 |
| 58 | −1 | 180 |
| 59 | −2 | 90 |
| 60 | 6 | 280 |
| 61 | 12 | 440 |
| 62 | 7 | 375 |
| 63 | 20 | 62 |
| 64 | −24 | 24 |
| 65 | −4 | 56 |
| 66 | 0 | 700 |
| 67 | −2 | 1200 |
| 68 | 14 | 9 |
| 69 | 0 | 120 |
| 70 | 0 | 400 |
| 71 | 10 | 205 |
| 72 | 8 | 150 |
| 73 | 16 | 60 |
| 74 | −6 | 35 |
| 75 | 13 | 360 |
| 76 | 11 | 20 |
| 77 | 0 | 140 |
| 78 | 4 | 1600 |
| 79 | 8 | 200 |
| 80 | 16 | 80 |
| 81 | 14 | 16 |
| 82 | −1 | 850 |
| 83 | 14 | 63 |
| 84 | −2 | 54 |
| 85 | 7 | 580 |
| 86 | 10 | 42 |
| 87 | 0 | 20 |
| 88 | 7 | 56 |
| 89 | −3 | 56 |
| 90 | 3 | 225 |
| 91 | 11 | 25 |
| 92 | 0 | 30 |
| 93 | −38 | 12 |
| 94 | 7 | 6 |

$$\theta = \frac{\sum_{n=1}^{i} S_i |\theta_i|}{\sum_{n=1}^{i} S_i}$$

$$\theta = 7$$

Figure 5:
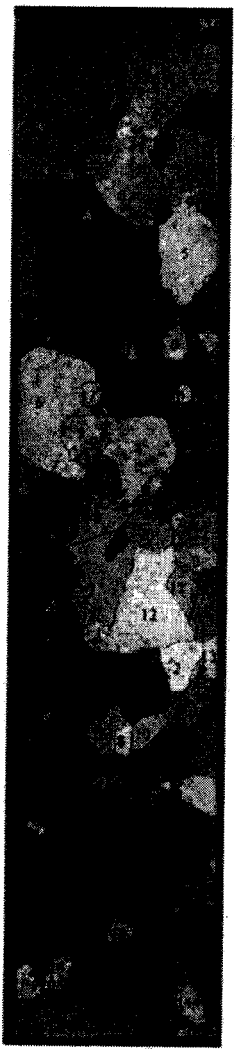
FIG. 5 illustrates the particulars and result of a specimen of embodiment 2 of the present invention (numbers labeled on crystal grains of the specimen are deviation angle $θ_i$ thereof).

See FIG. 5 and Table 4, the figure shows the particulars and result of the specimen of the embodiment 2 (numbers labeled on the crystal grains of the specimen are deviation angle $\theta_i$ of the crystal grains). As can be seen from the Table 4, deviation of magnetic property data detected by the present invention over magnetic property data detected by SST is merely 0.4%, which fully satisfies requirements for high precision detection.

TABLE 4

| | |
|---|---|
| Measured value $B_8$ (T) | 1.878 |
| Calculated value $B_8$ (T) | 1.885 |
| Deviation (%) | 0.4 |

What is claimed is:

1. A method for detecting an electromagnetic property, $B_8$, of an oriented silicon steel, the oriented silicon steel having a Si percentage content of 2.8~4.0%, the oriented silicon steel comprising crystal grains, the method comprising:

etching an etched pit into each of the crystal grains of the oriented silicon steel;

measuring, using a metallographic microscope and the etched pits, Euler angles of each of the crystal grains in the oriented silicon steel;

calculating an orientation deviation angle $\theta_i$ of each of the crystal grains using the respective Euler angles of each of the crystal grains;

calculating the electromagnetic property, $B_8$, using the following equation:

$$B_8 = -0.015 \times X \times \frac{\sum_{n=1}^{i} S_i |\theta_i|}{\sum_{n=1}^{i} S_i} + (B_0 - 0.04) \quad (1)$$

where $S_i$ is an area of each of the crystal grains, X is a correction coefficient of the element silicon, where X ranges from 0.1 T/degree to 10 T/degree and $B_0$ is a magnetic induction property of a single-crystal material.

* * * * *